US011501888B2

(12) United States Patent
Garcia

(10) Patent No.: US 11,501,888 B2
(45) Date of Patent: *Nov. 15, 2022

(54) RADIATION ATTENUATING PROTECTIVE GARMENTS

(71) Applicant: Operative Medical Solutions, LLC, Fort Worth, TX (US)

(72) Inventor: Nicolas Gabriel Garcia, Fort Worth, TX (US)

(73) Assignee: Operative Medical Solutions, LLC, Fort Worth, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/908,247

(22) Filed: Jun. 22, 2020

(65) Prior Publication Data

US 2020/0321137 A1    Oct. 8, 2020

Related U.S. Application Data

(63) Continuation-in-part of application No. 16/450,447, filed on Jun. 24, 2019, now Pat. No. 10,692,616, which is a continuation of application No. 15/444,299, filed on Feb. 27, 2017, now Pat. No. 10,332,644.

(60) Provisional application No. 62/299,967, filed on Feb. 25, 2016.

(51) Int. Cl.
*G21F 3/02* (2006.01)
*A61B 6/10* (2006.01)
*G21F 1/08* (2006.01)

(52) U.S. Cl.
CPC ............... *G21F 3/02* (2013.01); *A61B 6/107* (2013.01); *G21F 1/085* (2013.01)

(58) Field of Classification Search
CPC ............ G21F 3/02; G21F 1/085; A61B 6/107
See application file for complete search history.

(56) References Cited

U.S. PATENT DOCUMENTS

| | | | | |
|---|---|---|---|---|
| 5,103,504 A | * | 4/1992 | Dordevic | G21F 3/025 |
| | | | | 2/457 |
| 5,745,925 A | * | 5/1998 | Ghilardi | G21F 3/02 |
| | | | | 2/457 |
| 9,248,044 B2 | * | 2/2016 | Criss | A61F 5/4408 |
| 9,375,045 B2 | * | 6/2016 | Farris | A43B 23/0205 |
| 10,332,644 B2 | * | 6/2019 | Garcia | G21F 3/02 |
| 10,692,616 B2 | * | 6/2020 | Garcia | G21F 3/02 |
| 2005/0211930 A1 | * | 9/2005 | DeMeo | G21F 5/00 |
| | | | | 250/516.1 |
| 2005/0273903 A1 | * | 12/2005 | Rudman | A41D 27/28 |
| | | | | 2/69 |
| 2010/0163758 A1 | * | 7/2010 | Kirschenbaum | G21F 3/02 |
| | | | | 250/516.1 |
| 2012/0085943 A1 | * | 4/2012 | Spagnuolo | G21F 3/02 |
| | | | | 250/516.1 |

(Continued)

*Primary Examiner* — David A Vanore
(74) *Attorney, Agent, or Firm* — Decker A. Cammack

(57) ABSTRACT

A radiation-attenuation garment system having a plurality of radiation-attenuating material panels adapted to conform to the contours of a body. The radiation-attenuation garment system includes a shirt and underwear shorts formed by compression material. A plurality of radiation-attenuating material panels are removably disposed within the shirt and underwear shorts to protect the wearer from radiation exposure in the areas having the radiation attenuation panels.

22 Claims, 4 Drawing Sheets

(56) References Cited

U.S. PATENT DOCUMENTS

| | | | | |
|---|---|---|---|---|
| 2013/0095730 A1* | 4/2013 | Jensen | ................... | A41D 1/06 |
| | | | | 450/95 |
| 2015/0004131 A1* | 1/2015 | Milstein | ................. | G21F 3/025 |
| | | | | 250/516.1 |
| 2020/0321137 A1* | 10/2020 | Garcia | ..................... | G21F 3/02 |

* cited by examiner

RADIATION ATTENUATING PROTECTIVE GARMENTS

INCORPORATION BY REFERENCE TO ANY PRIORITY APPLICATION

Any and all applications for which a foreign or domestic priority claim is identified in the Application Data Sheet (either filed with the present application or subsequently amended) are hereby incorporated by reference under 37 CFR § 1.57. The present application is a continuation-in-part of U.S. patent application Ser. No. 16/450,447, filed Jun. 24, 2019. For clarity, the following are hereby incorporated by reference: U.S. patent application Ser. No. 15/444,299, filed Feb. 27, 2017, by the same inventor and with the same title, which claims priority to U.S. Provisional Patent Application Ser. No. 62/299,967, filed Feb. 25, 2016, by the same inventor and with the same title, and U.S. patent application Ser. No. 16/450,447, filed Jun. 24, 2019.

BACKGROUND OF THE INVENTION

Field of the Invention

The present invention relates generally to radiation attenuating material. More specifically, the present invention relates to radiation attenuating material for protection of the human body during medical procedures.

Background of the Invention

During a medical imaging procedure, the human body in exposed to radiation that can damage critical anatomy of the patient's body. In order to mitigate the risk of exposure to these important areas, the use of heavy lead aprons have been adapted for use in the imaging area. These heavy lead aprons are cumbersome for the patient, operating room personnel, and technicians involved in the X-Ray process in hospitals and surgery centers. The lead apron can slide off of the patient's body as the patient is contorted into the position that facilitates the best image acquisition. This can prevent the acquisition of an image of the intended anatomy, as well as expose the aforementioned sensitive anatomy. Additionally, the lead aprons worn by doctors and technicians can similarly slide out of place and expose sensitive anatomy to harm as they maneuver around the patient to provide treatment and image capture. Further, current lead aprons are expensive due to overuse of lead in areas where radiation protection is unnecessary. Accordingly, it is desirable to have a garment system that effectively protects a person's anatomy, while allowing ease of movement.

SUMMARY OF THE INVENTION

One embodiment of the invention includes a lightweight fabric with a built-in lead protection material. A radiation-attenuation garment system having a plurality of radiation-attenuating material panels adapted to conform to the contours of a body. The radiation-attenuation garment system includes a radiation attenuation shirt, comprising a front shirt portion, made of a compression material and a back shirt portion, made of a compression material. The front portion and the back portion are secured together to form a shirt, such that a first radiation-attenuating material panel may be removably disposed within the shirt, thereby protecting the wearer from radiation exposure in the areas having the radiation attenuation panels. The radiation-attenuation garment system may also include radiation-attenuation underwear shorts, comprising a front underwear shorts portion, made of a compression material and a back underwear shorts portion, made of a compression material. The front underwear portion and the back underwear portion may be secured together, or may be formed as a unitary garment (e.g., without seams) to form underwear shorts. A radiation-attenuating material panel may be removably disposed within the underwear shorts, thereby protecting the wearer from radiation exposure in the areas having the radiation attenuation panels. Other embodiments in accordance with the spirit and scope of the invention will become apparent to those of skill in the art.

DETAILED DESCRIPTION OF THE INVENTION

Figure 1:
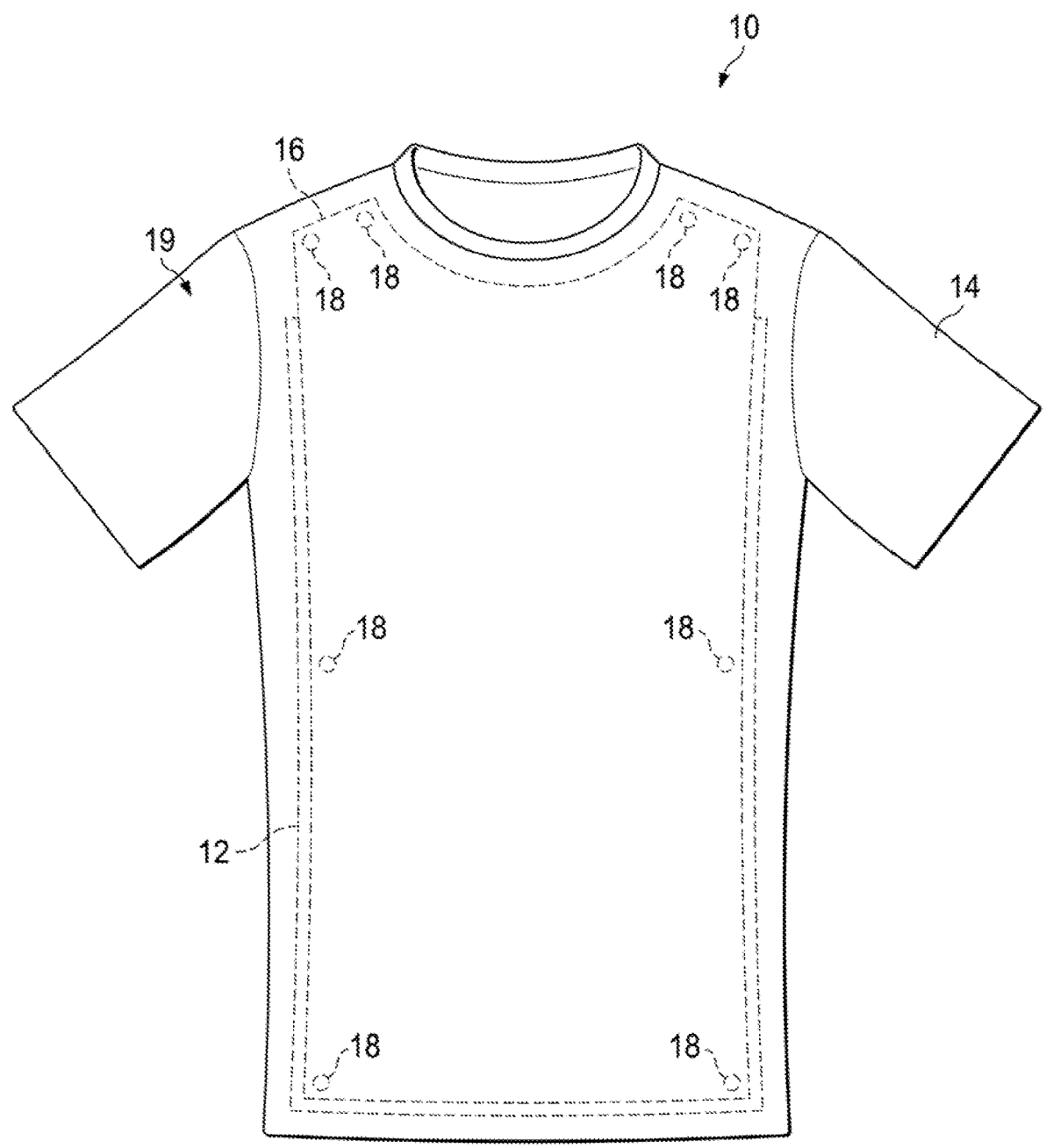
FIG. 1 shows a layered, front view of one embodiment of the radiation-attenuating shirt.

The present invention is directed to radiation-attenuating garments for medical personnel. FIG. 1 generally shows a layered, front view of one embodiment of the radiation-attenuating shirt. In FIG. 1, for example, there is shown a front shirt portion 19 of a radiation-attenuating shirt 10. The front shirt portion 19 is formed of compression fabric 14, such that the shirt 10 tightly adheres to a wearer and minimally restricts movement. Compression material 14 can be Spandex™, polyester blend, or any other material designed to stretch and retract such that a compression of the body is achieved. In another exemplary embodiment, compression material 14 can be a cooling, and/or moisture-wicking fabric, such as performance fabrics known in the art.

Front shirt portion 19 includes a first pocket 12, wherein the pocket is formed by attaching a panel of compression material to front shirt portion on the bottom and sides of the panel of compression material. The unattached top portion of the first pocket 12 allows an object to be inserted between the front shirt portion 19 and the panel of compression material and be retained thereby.

A radiation-attenuating material panel 16 prevents transmission of X-rays therethrough. Preferably, the radiation-attenuating material panel 16 is made of lead. However, the radiation attenuating material panel may also be a lead alloy or other material suitable to block or mitigate transmission of X-rays. Lead protection for direct beam 60 kV, 80 kV, 100 kV, and/or 0.5 millimeter lead equivalent is required for male and female reproductive parts. Lead protection for direct beam 60 kV, 80 kV, 100 kV, and/or 0.5 millimeter lead equivalent is required for male and female bone marrow. The radiation-attenuating material panels are adapted to conform to the contours of a body and can vary in size and shape to cover the requisite anatomy. Radiation-attenuating material panel 16 includes attaching mechanisms 18 on one of its sides.

Radiation-attenuating material panel 16 may be removably inserted into first pocket 12. However, due to the weight of the radiation-attenuating material panel 16, a plurality of attaching mechanisms 18 are utilized to help retain radiation-attenuating material panel 16. For example, attaching mechanism 18 can be a fastener system including grommeted snaps. Alternatively, the attaching mechanisms can include Velcro™, buttons, snaps, ties, buckles, or any other mechanism for allowing removably coupling the radiation-attenuating material panel 16 to the front shirt portion 19. The front shirt portion 19, includes a plurality of attaching mechanisms disposed on one side of the front portion to attach to the plurality of attaching mechanisms 18 on the radiation-attenuating material panel 16.

Figure 2:
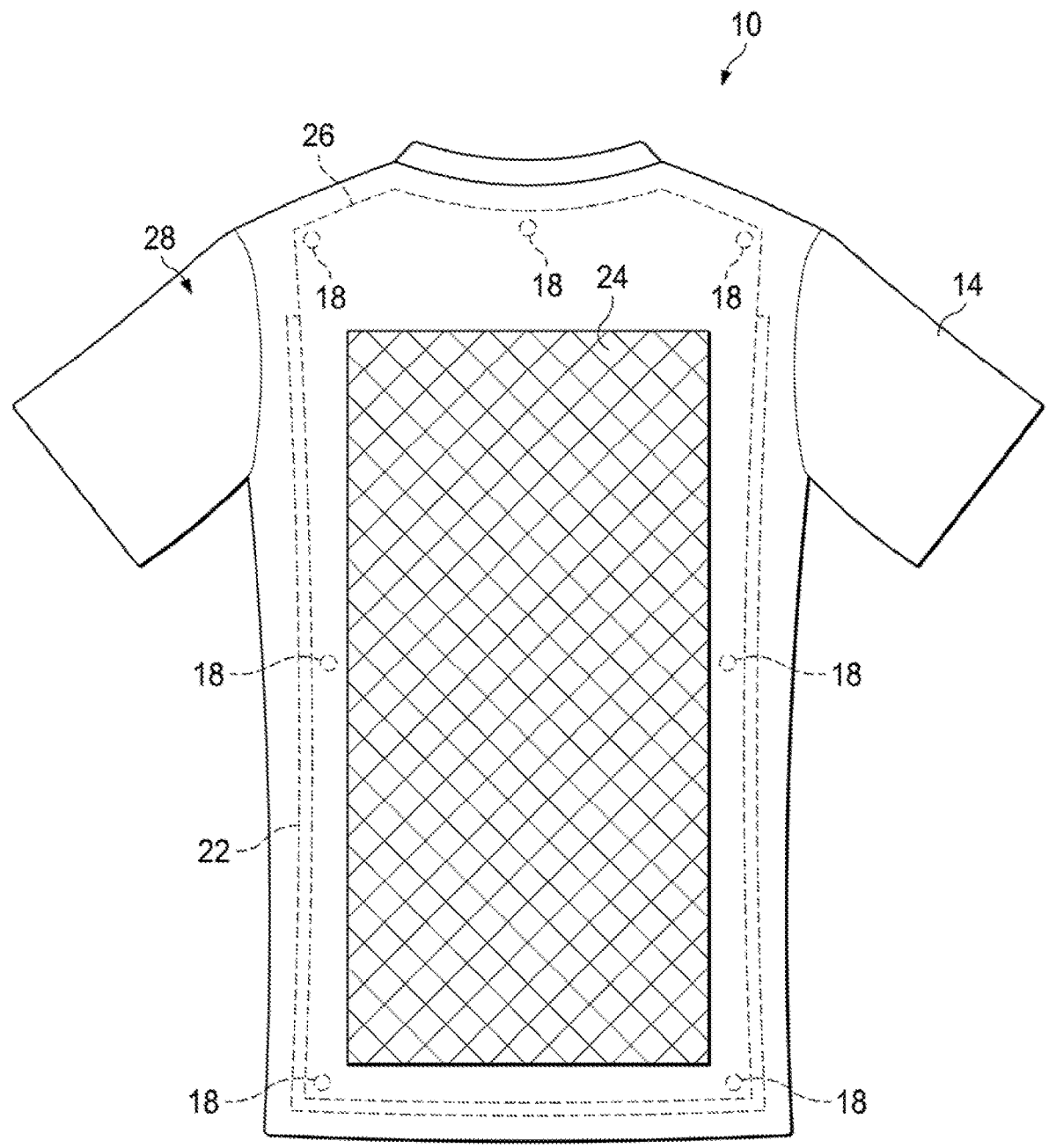
FIG. 2 shows a layered, rear view of one embodiment of the radiation-attenuating shirt.

Referring to FIG. 2, there is shown a layered, rear view of one embodiment of the radiation-attenuating shirt. In FIG. 2, for example, there is shown a back shirt portion 28 of a radiation-attenuating shirt 10. The back shirt portion 28 is formed of compression fabric 14, such that the shirt 10 tightly adheres to a wearer and minimally restricts movement. Compression material 14 can be Spandex™, polyester blend, nylon, or any other material designed to stretch and retract such that a compression of the body is achieved.

Back shirt portion 28 includes a second pocket 22, wherein the pocket is formed by attaching a panel of compression material to back shirt portion 28 on the bottom and sides of the panel of compression material. The unattached top portion of the second pocket 22 allows an object to be inserted between the back shirt portion 28 and the panel of compression material and be retained thereby.

A second radiation-attenuating material panel 26 prevents transmission of X-rays therethrough. Preferably, the second radiation-attenuating material panel 26 is made of lead. However, the second radiation attenuating material panel 26 may also be a lead alloy or other material suitable to block or mitigate transmission of X-rays. Second radiation-attenuating material panel 26 includes attaching mechanisms 18 on one of its sides and is optimally shaped and sized for a wearer's back.

Second radiation-attenuating material panel 26 can be removably inserted into second pocket 22. A plurality of attaching mechanisms 18 are utilized to help retain second radiation-attenuating material panel 26 in second pocket 22. For example, attaching mechanism 18 can be a fastener system including grommeted snaps. Alternatively, the attaching mechanisms can include Velcro™, buttons, snaps, buckles, ties, or any other mechanism for allowing removably coupling second radiation-attenuating material panel 26 to back shirt portion 28 and may also be operable to secure the second radiation-attenuating material panel 26 to the first radiation-attenuating material 16. The back shirt portion 28, includes a plurality of attaching mechanisms 18 disposed on one side of the front portion to attach to the plurality of attaching mechanisms 18 on second radiation-attenuating material panel 26.

Figure 3:
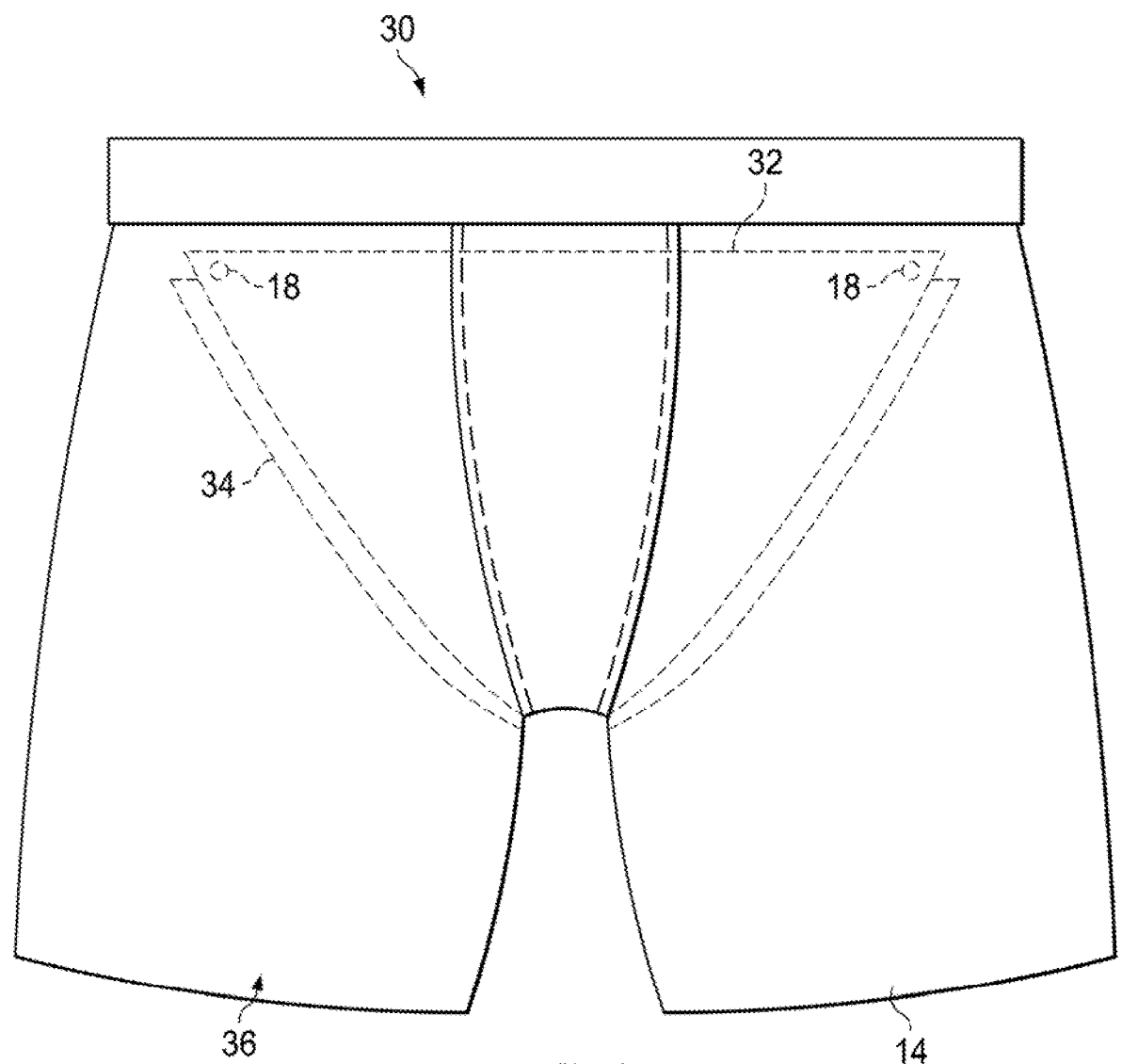
FIG. 3 shows a layered, front view of one embodiment of the radiation-attenuating underwear shorts.

FIG. 3 shows a layered, front view of one embodiment of the radiation-attenuating underwear shorts 30. In FIG. 3, for example, there is shown a front underwear portion 36 of radiation-attenuating underwear shorts 30. The front underwear portion 36 is formed of compression fabric 14, such that the underwear 30 tightly adheres to a wearer and minimally restricts movement. Compression material 14 can be Spandex™, polyester blend, or any other material designed to stretch and retract such that a compression of the body is achieved.

Front underwear portion 36 includes a first pocket 34, wherein the first pocket is formed by attaching a panel of compression material to front underwear portion 36 on the bottom and sides of the panel of compression material. The unattached top portion of the first pocket 34 allows an object to be inserted between the front underwear portion 36 and the panel of compression material allowing the object to be retained thereby.

A first radiation-attenuating material panel 32 prevents transmission of X-rays therethrough. Preferably, the first radiation-attenuating material panel 32 is made of lead. However, the first radiation-attenuating material panel 32 may also be a lead alloy or other material suitable to block or mitigate transmission of X-rays. First radiation-attenuating material panel 32 includes attaching mechanisms 18 on one of its sides and is optimally shaped and sized for a wearer's pelvis. Shapes may include derivations for male and female anatomy.

First radiation-attenuating material panel 32 can be removably inserted into first pocket 34. A plurality of attaching mechanisms 18 are utilized to help retain first radiation-attenuating material panel 32 in first pocket 34. For example, attaching mechanism 18 can be a fastener system including grommeted snaps. Alternatively, the attaching mechanisms can include Velcro™ buttons, or any other mechanism for allowing removably coupling first radiation-attenuating material panel 32 to front underwear portion 36. The front underwear portion 36, includes a plurality of attaching mechanisms 18 disposed on one side of the front portion to attach to the plurality of attaching mechanisms 18 on first radiation-attenuating material panel 32.

Figure 4:
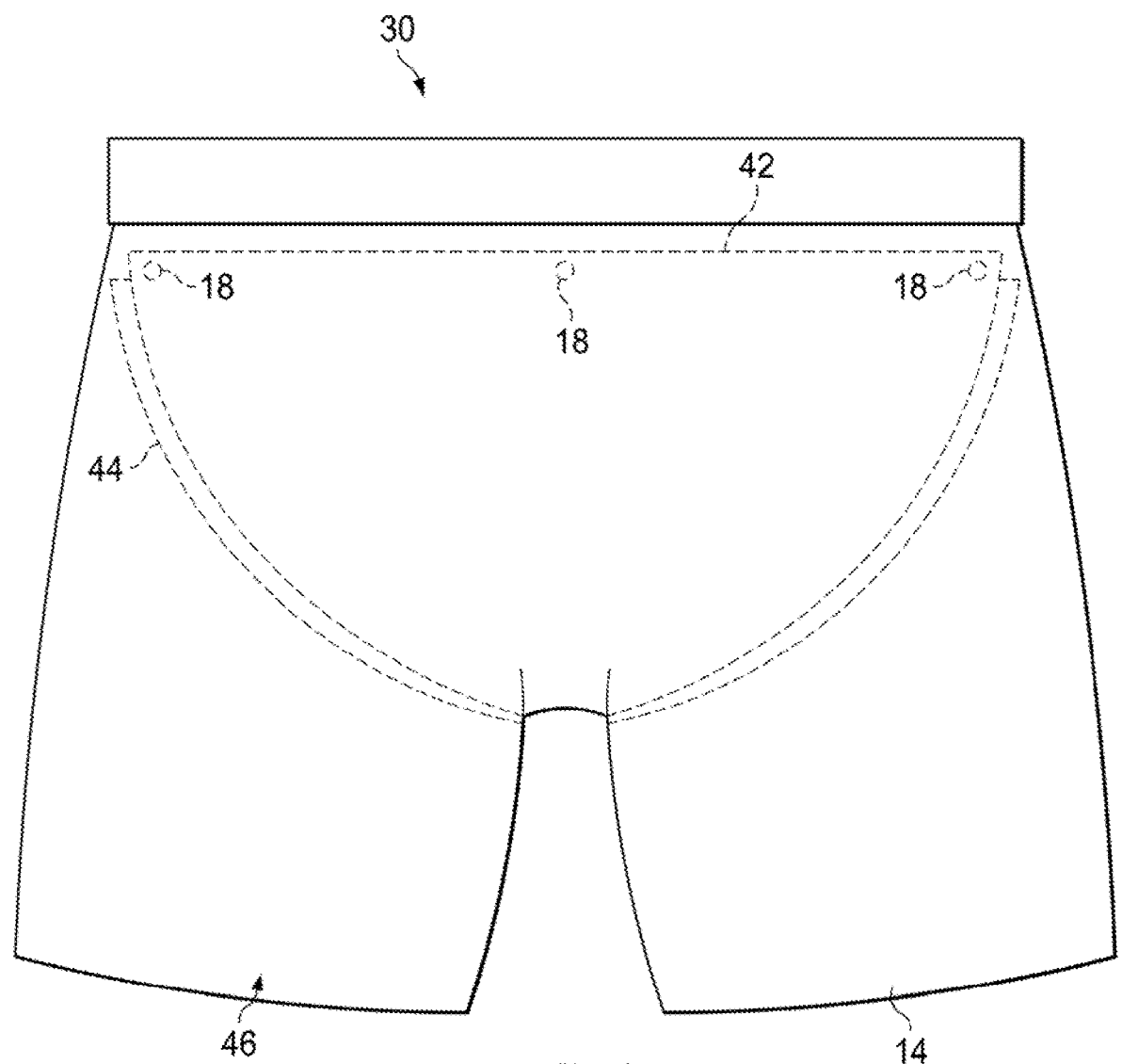
FIG. 4 shows a layered, rear view of one embodiment of the radiation-attenuating underwear shorts.

FIG. 4 shows a layered, rear view of one embodiment of the radiation-attenuating underwear shorts 30. In FIG. 4, for example, there is shown a back underwear portion 46 of radiation-attenuating underwear shorts 30. The back underwear portion 46 is formed of compression fabric 14, such that the underwear 30 tightly adheres to a wearer and minimally restricts movement. Compression material 14 can be Spandex™, polyester blend, or any other material designed to stretch and retract such that a compression of the body is achieved.

Back underwear portion 46 includes a second pocket 44, wherein the first pocket is formed by attaching a panel of compression material to back underwear portion 46 on the bottom and sides of the panel of compression material. The unattached top portion of the second pocket 44 allows an object to be inserted between the back underwear portion 46 and the panel of compression material allowing the object to be retained thereby.

A second radiation-attenuating material panel 42 prevents transmission of X-rays therethrough. Preferably, the second radiation-attenuating material panel 42 is made of lead. However, the second radiation-attenuating material panel 42 may also be a lead alloy or other material suitable to block or mitigate transmission of X-rays. Second radiation-attenuating material panel 42 includes attaching mechanisms 18 on one of its sides and is optimally shaped and sized for a wearer's pelvis.

Second radiation-attenuating material panel 42 can be removably inserted into second pocket 44. A plurality of attaching mechanisms 18 are utilized to help retain second radiation-attenuating material panel 42 in second pocket 44. For example, attaching mechanism 18 can be a fastener system including grommeted snaps. Alternatively, the attaching mechanisms can include Velcro™, buttons, or any other mechanism for allowing removably coupling second radiation-attenuating material panel 42 to back underwear portion 46. The back underwear portion 46, includes a plurality of attaching mechanisms 18 disposed on one side of the front portion to attach to the plurality of attaching mechanisms 18 on second radiation-attenuating material panel 42.

Advantageously, the second radiation-attenuating material is lighter and cheaper than current options. By compressing the radiation attenuating material to the wearer, the present invention provides greater protection against slippage and exposure of vulnerable anatomy.

While the present invention has been described in detail, it is not intended to be limited. Accordingly, various changes, variations, and substitutions may be made without departing with the scope of the invention as disclosed.

What is claimed is:

1. A radiation-attenuation shirt, comprising:
   a plurality of radiation-attenuating material panels adapted to conform to the contours of a body, having a plurality of attaching mechanisms on one side;
   a front portion, made of a compression material and having a plurality of attaching mechanisms disposed on one side of the front portion, the front portion including a first pocket for retaining a first radiation attenuating material panel; and
   a back portion, made of a compression material and having a plurality of attaching mechanisms disposed on one side of the back portion, the back portion including a second pocket for retaining a second radiation attenuating material panel,
   wherein the front portion and the back portion are secured together to form a shirt, such that the attaching mechanisms and the first and second pockets are disposed within the shirt,
   wherein the first radiation-attenuating material panel is removably disposed within the first pocket and the plurality of attaching mechanisms of the first radiation-attenuating material panel are removably coupled to the plurality of attaching mechanisms of the front portion,
   wherein the second radiation-attenuating material panel is removably disposed within the second pocket and the plurality of attaching mechanisms of the second radiation-attenuating material panel are removably coupled to the plurality of attaching mechanisms of the rear portion; and
   wherein the compression material comprises at least one of a moisture wicking or a cooling fabric.

2. The radiation-attenuation shirt of claim 1, wherein the radiation attenuating panels are comprised of lead.

3. The radiation-attenuation shirt of claim 1, wherein the radiation attenuating panels are comprised of lead alloy.

4. The radiation-attenuation shirt of claim 1, wherein the radiation attenuating panels are covered in a removable, machine washable material.

5. The radiation-attenuation shirt of claim 1, wherein the front portion and the back portion include a breathable mesh proximate to the radiation attenuating panels.

6. The radiation-attenuation shirt of claim 1, wherein the compression material is a moisture-wicking fabric.

7. The radiation-attenuation shirt of claim 1, wherein the compression material is a cooling fabric.

8. The radiation-attenuation shirt of claim 1, wherein the compression material is a moisture-wicking, cooling fabric.

9. Radiation-attenuation underwear shorts, comprising:
   a plurality of radiation-attenuating material panels adapted to conform to the contours of a body, having a plurality of attaching mechanisms on one side;
   a front portion, made of a compression material and having a plurality of attaching mechanisms disposed on one side of the front portion, the front portion including a first pocket for retaining a first radiation attenuating material panel; and
   a back portion, made of a compression material and having a plurality of attaching mechanisms disposed on one side of the back portion, the back portion including a second pocket for retaining a second radiation attenuating material panel,
   wherein the front portion and the back portion are secured together to form underwear shorts, such that the attaching mechanisms and the first and second pockets are disposed within the underwear shorts,
   wherein the first radiation-attenuating material panel is removably disposed within the first pocket and the plurality of attaching mechanisms of the first radiation-attenuating material panel are removably coupled to the plurality of attaching mechanisms of the front portion,
   wherein the second radiation-attenuating material panel is removably disposed within the second pocket and the plurality of attaching mechanisms of the second radiation-attenuating material panel are removably coupled to the plurality of attaching mechanisms of the rear portion, and
   wherein the compression material comprises at least one of a moisture wicking or a cooling fabric.

10. The radiation-attenuation underwear shorts of claim 9, wherein the radiation attenuating panels are comprised of lead.

11. The radiation-attenuation underwear shorts of claim 9, wherein the radiation attenuating panels are comprised of lead alloy.

12. The radiation-attenuation underwear shorts of claim 9, wherein the radiation attenuating panels are covered in a removable, machine washable material.

13. The radiation-attenuation underwear shorts of claim 9, wherein the compression material is a moisture-wicking fabric.

14. The radiation-attenuation underwear shorts of claim 9, wherein the compression material is a cooling fabric.

15. The radiation-attenuation underwear shorts of claim 9, wherein the compression material is a moisture-wicking, cooling fabric.

16. A radiation-attenuation garment system, comprising:
    a plurality of radiation-attenuating material panels adapted to conform to the contours of a body;
    a radiation attenuation shirt, comprising:
    a front shirt portion, made of a compression material; and
    a back shirt portion, made of a compression material,
    wherein the front portion and the back portion are secured together to form a shirt, such that a first radiation-attenuating material panel is removably disposed within the shirt;
    radiation-attenuation underwear shorts, comprising:
    a front underwear portion, made of a compression material; and
    a back underwear portion, made of a compression material,
    wherein the front underwear portion and the back underwear portion are secured together to form underwear shorts, such that a first radiation-attenuating material panel is removably disposed within the underwear shorts, and
    wherein the compression material comprises at least one of a moisture wicking or a cooling fabric.

17. The radiation-attenuation garment system of claim 16, wherein the radiation attenuating panels are comprised of lead.

18. The radiation-attenuation garment system of claim 16, wherein the radiation attenuating panels are comprised of lead alloy.

19. The radiation-attenuation garment system of claim 16, wherein the radiation attenuating panels are covered in a removable, machine washable material.

20. The radiation-attenuation garment system of claim 16, wherein the compression material is a moisture-wicking fabric.

21. The radiation-attenuation garment system of claim 16, wherein the compression material is a cooling fabric.

22. The radiation-attenuation underwear shorts of claim 16, wherein the compression material is a moisture-wicking, cooling fabric.

* * * * *